United States Patent [19]

Pujado

[11] 4,246,191
[45] Jan. 20, 1981

[54] AMMOXIDATION PROCESS

[75] Inventor: Peter R. Pujado, Palatine, Ill.

[73] Assignee: UOP Inc., Des Plaines, Ill.

[21] Appl. No.: 65,827

[22] Filed: Aug. 13, 1979

[51] Int. Cl.$^3$ ............................................ C07C 120/14
[52] U.S. Cl. .................................. 260/465.3; 260/464
[58] Field of Search ................. 260/465.3, 465 C, 464

[56] References Cited

U.S. PATENT DOCUMENTS

| | | | |
|---|---|---|---|
| 3,472,892 | 10/1969 | Callahan et al. | 260/465.3 |
| 3,501,517 | 3/1970 | Hughes et al. | 260/465.3 X |
| 3,639,103 | 2/1972 | Sheely | 260/465.3 X |
| 3,644,472 | 2/1972 | Paleologo et al. | 260/465.3 |
| 3,819,679 | 6/1974 | Sheely | 260/465.3 |
| 4,102,914 | 7/1978 | Beuther et al. | 260/465.3 |

*Primary Examiner*—Joseph Paul Brust
*Attorney, Agent, or Firm*—James R. Hoatson, Jr.; John F. Spears, Jr.; William H. Page, II

[57] ABSTRACT

A process for the ammoxidation of olefinic hydrocarbons in a fluidized reactor is disclosed. The upper level of the fluidized catalyst bed is maintained near the inlet of the particle separator located at the top of the reactor. This reduces the temperature variation and homogeneous reactions within the reactor and also increases the useful life of the catalyst.

6 Claims, 1 Drawing Figure

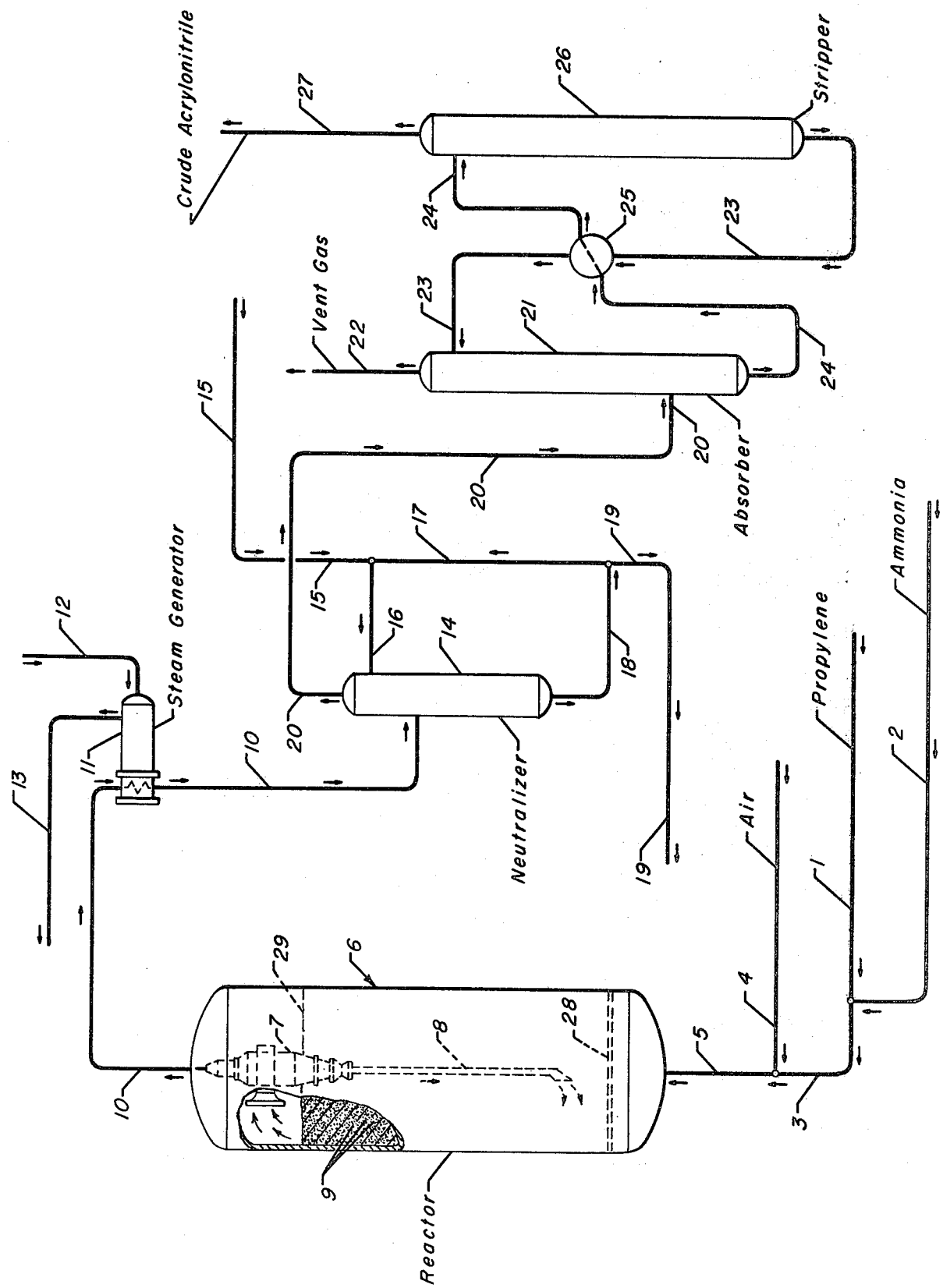

AMMOXIDATION PROCESS

FIELD OF THE INVENTION

The invention relates to a hydrocarbon conversion process. The invention more specifically relates to an improved process for the ammoxidation of olefinic hydrocarbons to the corresponding nitriles in a reaction zone containing a fluidized catalyst bed. The invention is specifically directed to the size and level of the fluidized catalyst bed within the reaction zone. References concerned with similar subject matter are concentrated in Class 260, especially Class 260-465, and in Class 23-288.

PRIOR ART

The overall flow of a representative process for the production of acrylonitrile by the ammoxidation of propylene is described in an article at page 80 of the Mar. 20, 1972 edition of *Chemical Engineering* and in an article at page 171 of the June 6, 1977 edition of *The Oil and Gas Journal*. These references illustrate the entire flow scheme of an ammoxidation process including the various product recovery and purification steps.

Catalysts which may be used in the ammoxidation process are described in U.S. Pat. Nos. 2,904,580 (Cl. 260-465.3), 3,230,246 (Cl. 260-465.3), 3,186,955 (Cl. 252-435), 3,197,419 (Cl. 252-456), 3,198,750 (Cl. 252-456), 3,200,081 (Cl. 252-443), 3,200,084 (Cl. 252-462), 3,446,833 (Cl. 260-465.3), 3,446,834 (Cl. 260-465.3) 3,686,295 (Cl. 260-533N) and 3,892,794 (Cl. 260-465.3). These patents also provide general descriptions of the reactants, operating conditions and operating procedures of the ammoxidation process.

The regeneration of ammoxidation catalysts is the general subject of U.S. Pat. Nos. 3,882,159 (Cl. 260-465.3) and 4,053,333 (Cl. 252-416). The former reference teaches the benefits of adding an inert support material containing molybdenum during the regeneration of molybdenum containing oxidation catalysts. The latter reference attributes beneficial regeneration results to the heating of the catalyst in an atmosphere which comprises 20-45% by volume of steam, with the balance being air or inert gas.

U.S. Pat. No. 3,691,224 (Cl. 260-465.3) describes the regeneration of ammoxidation catalysts within the dip leg or exhaust tube through which catalyst descends from the cyclone used at the top of the reactor. U.S. Pat. No. 3,230,246 (Cl. 260-465.3) describes an ammoxidation reactor and various elements which may be used within the reactor. U.S. Pat. No. 3,644,472 (Cl. 260-465.3) presents an ammoxidation process utilizing finned heat removal tubes to divide the fluidized catalyst bed into smaller beds, each of which has a height to diameter ratio between 5:1 and 20:1.

U.S. Pat. Nos. 3,472,892 (Cl. 260-465.3), 3,501,517 (Cl. 260-465), 3,639,103 (Cl. 23-288S) and 3,819,679 (Cl. 260-465.3) all present diagrams of reaction zones for the ammoxidation process. These references teach the use of a disengagement zone above the dense bed of fluidized catalyst or the use of a quench zone above the reaction zone. It is believed these references do not teach or suggest the use of a fluidized catalyst bed having an upper interface located close to the inlet of the particle separator located at the top of the reaction zone. It is also believed these references do not teach the practice or benefits of maintaining a near constant temperature within the upper half of the reaction zone or the use of the fluidized catalyst bed to maintain this temperature profile.

BRIEF DESCRIPTION OF THE INVENTION

The invention provides an improved ammoxidation process which significantly increases the useful life of the fluidized catalyst. One embodiment of the invention may be broadly characterized as a process for the ammoxidation of olefinic hydrocarbons which comprises the steps of passing a feed stream comprising a $C_3$-$C_8$ unsaturated hydrocarbon into the lower one-half of a reaction zone which is maintained at ammoxidation conditions; passing an oxygen-containing gas and ammonia into the lower one-half of the reaction zone; fluidizing a single dense bed of catalyst within the reaction zone, with the catalyst bed extending upward to within less than 1.0 meter from the inlet of a particle separation zone located at the top of the reaction zone; passing a vapor stream collected in the upper one-half of the reaction zone and comprising an unsaturated nitrile and entrained catalyst particles into the particle separation zone, and separating catalyst from the vapor stream to form an effluent stream; and recovering the unsaturated nitrile from the effluent stream.

The improvement is associated with the maintenance of a rather uniform temperature at most points within the reaction zone. The temperature variation should be less than 20 centigrade degrees at all points between the midpoint of the catalyst bed and the inlet of the particle separation zone. The fluidized catalyst is used as a heat transfer medium which reduces temperature variations within the reaction zone.

BRIEF DESCRIPTION OF THE DRAWING

The Drawing illustrates one embodiment of the invention. A stream of propylene from line 1 is admixed with a stream of ammonia from line 2 and passed into line 3. The contents of line 3 are admixed with a stream of air from line 4 to form a vapor-phase feed stream which is passed into the reactor 6 through line 5. The feed stream passes upward through a porous grid 28 or other vapor distributor located near the bottom of the reactor and rises through a bed of fluidized catalyst 9 located within the reactor. The fluidized catalyst is maintained as a dense phase bed having an upper surface or interface 29 which is in close proximity to the inlet of the cyclone 7 utilized as a particle separation zone.

A vapor stream containing a considerable amount of entrained catalyst and the product acrylonitrile is collected at the top of the reaction zone and passed into the cyclone 7. Substantially all of the catalyst is separated from this vapor stream and returned to the fluidized catalyst bed through the vertical conduit 8. The acrylonitrile is removed from the reactor in a reaction zone effluent stream transported within line 10. Water from line 12 is transformed into steam which is removed through line 13 in a heat exchanger 11 used to cool the reaction zone effluent stream.

The reaction zone effluent stream is then passed into a neutralizer 14. Sulfuric acid is added through line 15 and passed through line 16 in admixture with recirculated liquid from line 17. This removes any excess ammonia which may be present and produces an aqueous ammonium sulfate solution carried by line 18 and withdrawn at a rate equal to its production rate through line 19. The remaining vapor stream carries the acrylonitrile into an absorber 21 through line 20. Carbon oxides, unreacted propylene, nitrogen, water vapor and some impurities are removed as a vent gas stream carried by line 22. The acrylontrile, hydrogen cyanide, acetonitrile and other organic impurities are absorbed into downward flowing water and removed in a liquid stream carried by line 24. This stream is heated in heat exchanger 25 and passed into the stripper 26. Steam stripping the entering liquid produces a bottoms stream which is cooled and passed into the absorber through line 23. The overhead vapor of the stripper is condensed in a means not shown and decanted to produce a net overhead liquid comprising the product acrylonitrile and some organic impurities which is removed in line 27.

DETAILED DESCRIPTION

Ammoxidation processes are used commercially to produce unsaturated nitriles from olefinic hydrocarbons. The most widely practiced of these processes is the ammoxidation of propylene in a fluidized bed reactor to produce acrylonitrile. The catalyst used in these processes suffers from gradual deactivation, which is attributed to the reduction of the oxidized metals contained in the catalyst to less highly oxidized states. It is believed that highly oxidized metals are necessary in highly active catalyst because oxygen from the catalyst is consumed in the ammoxidation reaction, with the catalytic metals then being reoxidized by the oxygen which is charged to the reaction zone. The catalyst remains relatively "clean" while it is being used. Coke deposition on the catalyst is therefore not a problem as it is in some fluidized bed processes such as the fluidized catalytic cracking of petroleum fractions. The gradual deactivation of the ammoxidation catalyst is, however, still an important operating and economic factor in ammoxidation processes.

It is an objective of the subject invention to provide an improved fluidized bed ammoxidation process. It is a further objective of the subject invention to provide a process for the production of acrylonitrile by the reaction of propylene, ammonia and oxygen in a reaction zone containing a fluidized bed of catalyst.

The feed hydrocarbon passed into the reaction zone may be any readily vaporizable olefinic hydrocarbon. As used herein, the term "olefinic hydrocarbon" is intended to include both cyclic and acyclic olefins. Common feed hydrocarbons are propylene for the production of acrylonitrile and isobutylene for the production of methacrylonitrile. Other olefinic hydrocarbons which may be charged to the subject process include butene-1, butene-2, methylisobutylene, pentenes, 3-methylbutene-1, hexene-1, hexene-2, 4-methylpentene-1, 2,3-dimethylbutene-1, octenes, cyclopentene, cyclohexene, and other homologs of these olefinic hydrocarbons.

The feed hydrocarbon is passed into a reaction zone and admixed with the oxygen and ammonia. This admixture of the three reactants can be achieved in several different sequences. Preferably, the hydrocarbon and ammonia are admixed with at least some of the oxygen prior to passage of the reactants into the reaction zone. Another method is to admix the hydrocarbon and ammonia and then pass this bi-component mixture into the reaction zone, with the oxygen entering the reaction zone separately. It is also possible for the hydrocarbon and air to be distributed within the reaction zone at more than one location. The majority of the reactants is preferably passed upward into the catalyst bed through a porous grid which extends across the interior of the reactor near the bottom of the reactor. The preferred grid has coverings directly over the vapor passageways, as in bubble caps used in fractionation columns, to aid in retaining the catalyst above the grid. Care must be taken to avoid the formation of an explosive mixture at any location at which there is not sufficient catalyst present to suppress an explosion. It is highly preferred that a portion of the air is passed into the reaction zone at a point within the catalyst bed to avoid forming an explosive mixture in the feed line.

The reaction zone is preferably in the shape of a vertically oriented closed cylinder which is not enlarged at the top. Since the ammoxidation reaction is highly exothermic, indirect heat exchange means are preferably provided at several points within the reaction zone at points which are within the fluidized mass of catalyst. The preferred heat removal medium is water, which is converted to steam used within various product recovery steps. Further details on the removal of heat from the reaction zone may be obtained by reference to U.S. Pat. No. 3,991,096.

For reasons of economy, the preferred source of the oxygen consumed within the reaction zone is air. However, other oxygen-containing gas streams including relatively pure oxygen streams may also be charged to the reaction zone.

While the process is being performed, the reaction zone is maintained at ammoxidation conditions. The pressure within the reaction zone is normally maintained within the range of from atmospheric to about 6.0 atmospheres gauge, with a pressure less than 2.0 atmospheres gauge being preferred. The average temperature required within the reaction zone will be dependent on such variables as the catalyst, the present catalyst activity, the desired conversion rates and the particular hydrocarbon being charged to the process. A general range of temperatures is from about 333° C. to 550° C. A preferred range of temperatures is from 420° C. to 480° C., with temperatures of about 440° C. being especially preferred. The space velocity of the olefinic hydrocarbon through the reaction zone should be within the range of from about 0.075 to about 0.15 kg of hydrocarbon per kilogram of catalyst per hour. The linear gas velocity within the reaction zone should be between about 25 to 60 cm/sec based on the cross-sectional area of an empty reaction zone.

The amounts of both oxygen and ammonia charged to the reaction zone are preferably in slight excess of those consumed within the reaction zone. The ammoxidation of the olefinic hydrocarbon is not totally selective and some of the hydrocarbon may be consumed in side reactions. The ammonia is not consumed in these reactions or by the products of these reactions. It may therefore not be necessary to supply more ammonia than hydrocarbon to the reaction zone. The molar ratio of hydrocarbon to ammonia is preferably between 1:0.90 and 1:1.15. The molar ratio of hydrocarbon to oxygen is preferably within the range of from 1:1 to about 1:1.5. The use of a lower ammonia feed rate achieved by the recycling of HCN to the reaction zone is taught in U.S. Pat. No. 3,819,679.

The catalyst should be readily fluidizable at the ammoxidation conditions maintained within the reaction zone. Catalysts having particle sizes up to 1,000 microns may be used, but the average particle size is preferably between 20 to 150 microns. The catalyst is retained within a single fluidized bed which occupies the great majority of the reaction zone. The catalyst bed is not divided into zones or sub-beds by foraminous members, grates or screens.

In the practice of the subject invention, the height of the upper portion of the catalyst bed is raised above that employed in the prior art. More precisely stated, only a very limited disengagement zone or volume is provided at the top of the reactor. The purpose of this is to maintain the gases in contact with a significant amount of catalyst until the gases enter the particle separation zone. By maintaining the gases in contact with catalyst, the rate of homogeneous reactions in which the olefinic hydrocarbon reacts with oxygen is reduced. These reactions consume the olefinic hydrocarbon and produce low value carbon oxides. A second adverse effect of allowing these reactions to occur at an appreciable rate is caused by their high exothermicity. The heat released by these reactions raises the temperature of the reactants and whatever catalyst is present. The combination of high temperatures and oxygen-consuming reactions causes the reduction of the metals in the catalyst, which deactivates the catalyst. The present invention has been shown to greatly increase the useful life of the catalyst by decreasing its rate of deactivation. This has extended the useful life of the catalyst between regenerations to from two to four times as long as was previously experienced.

The catalyst which is present within the volume of the reaction zone near the particle separation zone acts to decrease the rate of the homogeneous reactions and also serves as a highly efficient heat transfer medium. The presence of the catalyst therefore tends to equilibrate the temperatures in this part of the reaction zone with the average temperature of the rest of the reaction zone. For this reason, the presence of the desired amount of catalyst in the upper levels of the reaction zone may be determined by an examination of the temperature profile which exists along a line extending upward through the reaction zone to these upper levels. The temperature profile is preferably taken along a line extending from the midpoint of the catalyst bed to the inlet of the particle separation zone. If a feed or quench inlet or other temperature adjusting means is located at or near the midpoint of the catalyst bed, then the lower point at which the temperature begins is altered to a point more representative of the average temperature of the catalyst bed. The deviation along this temperature profile is to be less than about 20 centigrade degrees and is preferably less than 15 centigrade degrees.

The desired height of the catalyst bed may be described by reference to the catalyst density at various levels in the reaction zone. The inventive concept may therefore be described by reference to the transport disengagement height (TDH) which is determined by measurement of the catalyst concentration at several elevations at and above the dense-phase catalyst bed. In the practice of the subject invention, the TDH is above the inlet of the particle separation zone. In the normal nomenclature of fluidized reactor design, this is the same as the particle separation zone having a negative freeboard. The interface which marks the upper interface or surface of the dense phase of the fluidized catalyst is preferably no lower than a point 2.0 meters below the lowest part of the inlet of the particle separation zone. More preferably, this interface is less than 1.0 meter below the particle separation zone inlet. Depending on the design of the particle separation zone in particular and the rest of the reaction zone in general, the dense phase catalyst interface may be at or above the level of particle separation zone inlet.

To achieve the higher catalyst bed levels of the present invention it is necessary to expand the catalyst bed by increasing the gas flow rate of the reactants through the catalyst bed. The hydrocarbon feed rate to the process must therefore be increased. In order to maintain an appropriate space velocity in the fluidized bed (preferably between 0.09 and 0.12) at the higher feed rate the total amount of catalyst which is present in the reaction zone must be increased in a direct proportion to the increase in the flow rate of the reactant. The end result is that the capacity of the reaction zone is increased by between 10 to about 50%. The inventive concept therefore improves the process in two different ways: both the productive capacity of the process and the useful life of the catalyst are increased.

Most existing fluidized bed reactors for the ammoxidation of olefins have been designed for operation with a bubbling bed of catalyst. These reactors may have been designed for superficial gas velocities of about 30 cm/second. Because of mechanical limitations in the catalyst particle separation and recirculation system (even if there is no significant heat removal limitation), the possible increase in the capacity of such reactors is limited by the superficial gas velocity (normally between 40 and 60 cm/sec) that raises the catalyst interface or disengagement zone to a point close to the inlet of the cyclone of other particle separation means. This limitation must be observed to avoid an excessive catalyst entrainment through the cyclone, which in turn could result in undesirable catalyst losses or in the choking of the dipleg or standpipe of the cyclone. These mechanical limitations normally will not allow for the catalyst interface or disengagement zone to be closer than about 1 meter from the inlet of the cyclone. This mechanical limitation need not exist in newer reactors designed on the basis of higher catalyst densities in or about the inlet of the cyclone. Operation of such reactors has shown that superficial gas velocities in excess of 100 cm/second can be employed, with a preferred range being from about 40 to 90 cm/second. Operation at these higher velocities results in the entrance of such sizable amounts of fluidized catalyst into the cyclone that a catalyst circulation means of the type normally associated with the design of a "fast" fluidized bed reactor should be provided in order to maintain a satisfactory catalyst loading and circulation throughout the reaction zone.

In a typical fluidized reactor the catalyst entrained into the first stage cyclone was measured at approximately 27 lbs/sec. at a superficial gas velocity of 40 cm/sec. The quantity of entrained catalyst increased to about 132 lbs/sec. at a superficial gas velocity of 60 cm/sec. At the same time, the distance between the catalyst interface and the inlet of the cyclone decreased from about 9 meters to about 3 meters. The quantity of entrained catalyst in the vapors entering the cyclone was determined to increase from about 0.004 g/cm$^3$ to about 0.14 g/cm$^3$. In a separate experiment conducted under similar circumstances, the temperature in the upper portion of the reaction volume decreased from between 490°–520° C. at a superficial gas velocity of 30 cm/sec. to less than 460° C. at gas velocities of from 45 to 50 cm/sec. while the temperature in the dense phase portion of the fluidized bed remained between about 440°–445° C. at all times.

One embodiment of the invention may be characterized as a process for the ammoxidation of olefinic hydrocarbons which comprises the steps of passing a feed stream comprising a $C_3$-$C_8$ unsaturated hydrocarbon into the lower one-half of a reaction zone which is maintained at ammoxidation conditions including a temperature between 200° C. and 600° C.; passing an oxygen-containing gas and ammonia into the lower one-half of the reaction zone; fluidizing a single bed of ammoxidation catalyst within the reaction zone, with the fluidized catalyst bed having a dense phase which extends upward to a point within less than 2.0 meters of the inlet of a particle separation zone located at the top of the reaction zone; passing a vapor stream collected in the upper one-half of the reaction zone and comprising an unsaturated nitrile and entrained catalyst particles into the particle separation zone, and separating the majority of the entrained catalyst from the vapor stream to thereby produce a reaction zone effluent stream comprising the unsaturated nitrile; and recovering the unsaturated nitrile from the reaction zone effluent stream.

Another embodiment of the invention may be characterized as a process for the ammoxidation of olefinic hydrocarbons which comprises the steps of passing a feed stream comprising a $C_3$-$C_8$ unsaturated hydrocarbon and ammonia into the lower one-half of a reaction zone which is maintained at ammoxidation conditions including a temperature between 200° C. and 600° C.; passing an oxygen-containing gas stream into the lower one-half of the reaction zone; fluidizing a single bed of ammoxidation catalyst within the reaction zone, with the catalyst being fluidized to the extent that the temperature profile from the midpoint of the catalyst bed to the inlet of a particle separation zone located at the top of the reaction zone has a variation of less than 20 centigrade degrees; passing a vapor stream collected in the upper one-half of the reaction zone and comprising an unsaturated nitrile and entrained catalyst particles into the particle separation zone, and separating the majority of the entrained catalyst from the vapor stream to thereby produce a reaction zone effluent stream comprising the unsaturated nitrile; and recovering the unsaturated nitrile from the reaction zone effluent stream.

The particle separation zone is preferably one or more multiple stage cyclones. A two- or three-stage cyclone is preferred. Any other type of solid-vapor separation device of suitable efficiency and reliability may be employed if desired. The particles which enter the separation zone should be returned to the catalyst bed through a conduit which delivers the catalyst within the dense-phase portion of the catalyst bed.

The catalysts which may be employed have been well described in the available prior art including those references cited above. Ammoxidation catalysts are normally composed of several metals in the form of their oxides. The catalyst may or may not include a support material. A preferred support material is silica and if employed would comprise about 75 wt.% of the catalyst. The preferred catalyst contains at least one metallic component chosen from the group consisting of molybdenum, phosphorus, bismuth, antimony, iron, nickel and copper. More preferably, the catalyst also contains at least one metallic component chosen from the group consisting of tungsten, vanadium, cerium, bismuth, tin, tellurium, rhenium and cobalt.

I claim as my invention:

1. In a process for the ammoxidation of $C_3$ to $C_8$ acyclic olefinic hydrocarbons wherein the olefinic hydrocarbons, an oxygen-containing gas and ammonia are passed into a reaction zone maintained at ammoxidation conditions including a temperature between 200° C. and 600° C. and are contacted with a dense fluidized bed of ammoxidation catalyst and a gaseous effluent stream is received by a particle separation zone located at the top of the reaction zone; the improvement which comprises maintaining within said reaction zone said dense fluidized bed of said ammoxidation catalyst which possesses an upper surface interface proximate to said particle separation zone wherein said upper level of said dense fluidized bed of ammoxidation catalyst within said reaction zone possesses a surface interface near to said inlet of said particle separation zone located at the top of the reaction zone and maintaining a temperature profile from the midpoint of the reaction zone to the inlet of the particle 2. A process for the ammoxidation of a $C_3$-$C_8$ acyclic olefinic hydrocarbons which comprises the steps of:
   (a) passing a feed stream comprising said $C_3$-$C_8$ acyclic olefinic hydrocarbon into the lower one-half of a reaction zone which is maintained at ammoxidation conditions including a temperature between 200° C. and 600° C.;
   (b) passing an oxygen-containing gas and ammonia into said lower one-half of the reaction zone;
   (c) fluidizing a single bed of ammoxidation catalyst within the reaction zone, with the fluidized catalyst bed having a dense phase which extends upward to a point proximate to the inlet of a particle separation zone located at the top of the reaction zone wherein the upper level of said dense phase of fluidized ammoxidation catalyst within said reaction zone possesses a surface interface near to said inlet of said particle separation zone located at the top of said reaction zone and maintaining a temperature profile from the midpoint of the reaction zone to the inlet of the particle separation zone having a variation of less than 20° C.;
   (d) passing a vapor stream collected in the upper one-half of the reaction zone and comprising an unsaturated nitrile and entrained catalyst particles into the particle separation zone, and separating the majority of the entrained catalyst from the vapor stream to thereby produce a reaction zone effluent stream comprising the unsaturated nitrile; and,
   (e) recovering the unsaturated nitrile from the reaction zone effluent stream.

3. The process of claim 2 further characterized in that the feed stream comprises propylene.

4. The process of claim 2 further characterized in that the feed stream comprises isobutylene.

5. The process of claim 2 further characterized in that the catalyst comprises at least one element chosen from the group consisting of molybdenum, phosphorus, antimony, iron, nickel and copper.

6. The process of claim 5 further characterized in that the catalyst comprises at least one element chosen from the group consisting of tungsten, vanadium, cerium, bismuth, tin, tellurium, rhenium and cobalt.

* * * * *